United States Patent [19]

Ishikawa

[11] 3,977,060

[45] Aug. 31, 1976

[54] APPARATUS FOR LOADING A MEDICAL NEEDLE HOLDER WITH A FILTER ELEMENT

[75] Inventor: Soji Ishikawa, Tokyo, Japan

[73] Assignee: Ishikawa Manufactory Company, Limited, Tokyo, Japan

[22] Filed: Sept. 19, 1975

[21] Appl. No.: 615,077

[30] Foreign Application Priority Data

Sept. 20, 1974   Japan.............................. 49-107710

[52] U.S. Cl. ............................ 29/33 S; 29/163.5 F; 29/200 R; 28/1.6; 425/383
[51] Int. Cl.² .................. B23P 23/00; B01D 27/02
[58] Field of Search ........... 29/33 R, 33 S, 163.5 F, 29/200 R, 208 R; 425/383; 28/1.6

[56] References Cited
UNITED STATES PATENTS

| | | |
|---|---|---|
| 3,515,282 | 6/1970 | Westesson................... 210/500 R X |
| 3,712,526 | 1/1973 | Hanousek et al. ................. 28/1.6 X |

Primary Examiner—Gil Weidenfeld
Attorney, Agent, or Firm—Haseltine, Lake & Waters

[57] ABSTRACT

Apparatus for loading a medical needle holder with a filter element consisting of a filament yarn, comprising a transport tube having yarn inlet and outlet ends, a yarn feed means for feeding a continuous filament yarn into the transport tube through the yarn inlet end thereof, yarn measuring and cutting means operative to cut the conveyed yarn in a predetermined length, needle holder retaining means for positioning a needle holder at the yarn outlet end of the transport tube and yarn transfer means for moving the cut segment of the yarn into a predetermined transitive position and from the transitive position into the needle holder.

16 Claims, 9 Drawing Figures

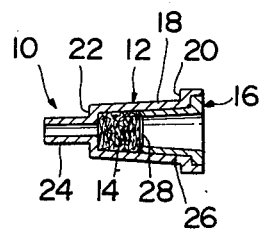
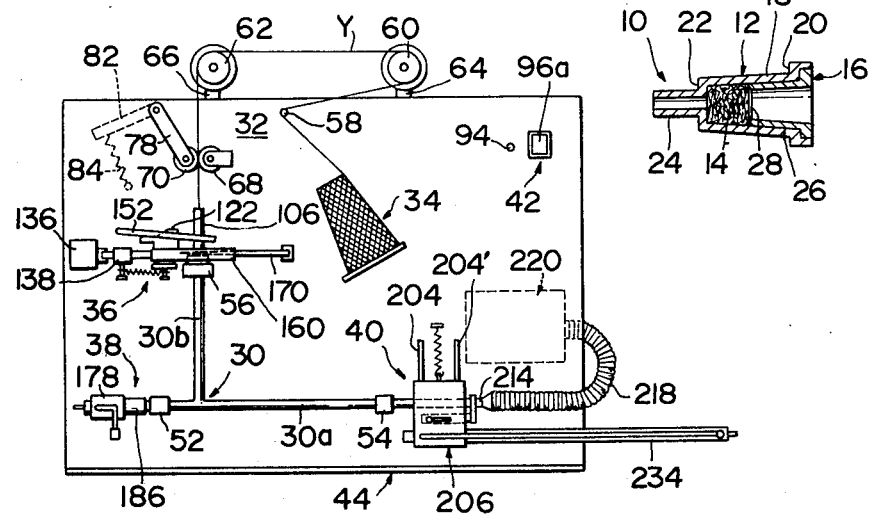
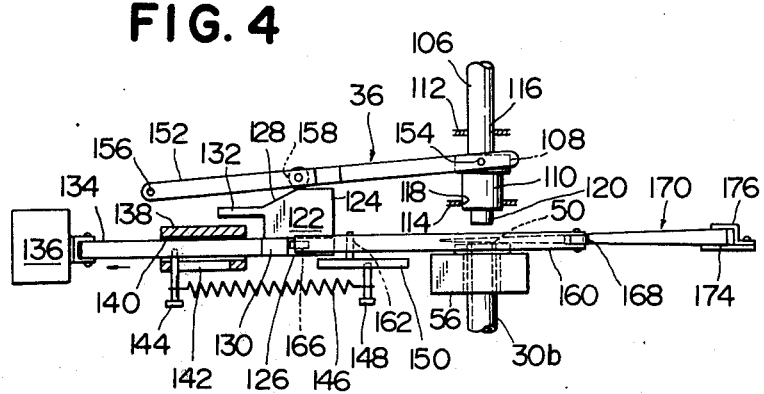

APPARATUS FOR LOADING A MEDICAL NEEDLE HOLDER WITH A FILTER ELEMENT

The present invention relates to an apparatus for mounting a filter element in a needle assembly for use in a medical administering device such as a hypodermic syringe or a venoclysis equipment for introducing a liquid medicament or transfusing blood into human body.

Extreme precautions are taken to prevent a parmaceutical preparation or blood for transfusion from being contaminated with impurities before the preparation or blood is injected into human body. Actually, however, there still exist various causes due to which impurities are present in or admixed to the preparation or blood before and even during an administering process. Impurities may happen to be introduced into a liquid medicament when, for example, an ampoule or other breakable container storing the medicament is punctured prior to injection or when a fluid conducting tube is being fitted to the rubber plug or a reservoir of a venoclysis equipment. The fine fragments of the punctured container or the fine particles of the rubber scraped from the plug of the venoclysis equipment may find their way through the administering system into the blood stream of the human body and may consequently injure the vascular tissues.

A variety of filter media have therefore been developed and found practical applications for the removal of impurities from liquid medicaments and blood for transfusion before the medicaments or blood are discharged from the needles or cannulae of the administering devices. One of the typical examples of the prior art filter media adapted to achieve this purpose is formed of staple fibers which are pressed or otherwise compacted into lump form and another example is formed of nylon fabrics or a mass of sintered nylon powder. The filter element is usually fitted into the passageway in the needle holder and collects impurities before the liquid medicament or the blood for transfusion is passed to the needle or cannula. When the medicament or blood flows through the filter element and consequently the filter element is subjected to the pressure of the flow, the filter element tends to be partly disintegrated and produce fine fragments of staple fibers, nylon fabrics or powder. This not only gives rise to deterioration of the collection efficiency of the filter element but is causative of production of secondary impurities although the majority of primary impurities initially contained in the medicament or blood directed into the needle holder may be collected by the filter element. The filter element thus provides in itself another important source of impurities in the medicament or blood and consequently fails to properly function as the filter medium.

With a view to solving these problems, I, the inventor, have proposed a new filter medium for a medical needle assembly in U.S. Pat. No. 3,859,999 dated Jan. 14, 1975 and assigned to Ishikawa Manufacturing Company, Limited, Tokyo, Japan. The filter medium disclosed in this issued patent comprises a wad of at least one length of continuous filament yarn of synthetic resin substantially uniformly entwined into the wad form and is located in a foremost end portion of the longitudinal passageway in the needle holder. The filament yarn constituting the filter element of such a filter medium is preferably produced by extruding a heat-plastified thermoplastic resin from a single extrusion orifice and is, for this reason, substantially free from the risk of being partly fractured or torn apart and producing fine fragments in the liquid passed through the filter medium even when the filter medium may be subjected to a forceful flow pressure. Because, furthermore, of the fact that the filter element is composed of a single filament yarn, the percentage of porosity of the filter medium made up of the filter element or elements can be readily and accurately controlled by selecting the thickness and/or the length of the yarn or yarns to constitute the filter medium depending upon the purpose for which the needle assembly is to be used. The filter medium is thus registering a marked commercial success in therapeutical circles for its guaranteed ability of collecting primary impurities contained in a dosage solution and for its freedom from the risk of producing secondary impurities.

In the process of manufacturing the needle assembly incorporating such a filter medium, however, it was found that difficulties are encountered in precisely locating and fixedly holding the filter element or elements within the needle holder. This is partly because of the extremely small space available in the needle holder and partly because of the inherently shapeless configuration of the filter element composed of the wad of the entwined filament yarn or yarns. If the filter element fails is to be precisely located within the needle holder assembly, then the filter element will form an obstacle to the movement of a syringe barrel or the adapter of a venoclysis equipment to which the needle holder assembly is to be fitted.

It is, therefore, an object of the present invention to provide an apparatus which is adapted to easily and precisely mount a filter element of the above described nature in a medical needle holder.

In accordance with the present invention, such an object will be basically accomplished in an apparatus which comprises a passage means having yarn inlet and outlet ends, yarn feed means for conveying a continuous filament yarn of synthetic resin from a yarn supply package and introducing the yarn into the passage means through the yarn inlet end thereof, yarn measuring and cutting means for measuring the length of the conveyed filament yarn and cutting the yarn in a predetermined length in each cycle of operation, needle holder retaining means for holding a generally tubular needle holder in a predetermined position having its open rearmost end located at the yarn outlet end of the passage means in each cycle of operation, and yarn transfer means for moving the cut segment of the filament yarn into a predetermined transitive position within the passage means and thereafter from the transitive position into the needle holder in the above mentioned predetermined position thereof through the yarn outlet end of the passage means.

The yarn measuring and cutting means may comprise detecting means for detecting the rate at which the filament yarn is fed into the passage means, signal generating means cooperative with the detecting means for producing a signal representative of the above mentioned predetermined length of the yarn fed into the passage means, guide means movable into and out of an operative position connected to the yarn inlet end of the passage means for guiding the yarn to the inlet end when moved into the operative position, cutting means having an operative position in proximity to the yarn inlet end of the passage means and biased toward an inoperative position withdrawn from the vicinity of the yarn inlet end, and actuating means biased to hold the guide means out of the operative position thereof and the cutting means in the inoperative position thereof and responsive to the signal from the aforesaid signal generating means for driving the guide means and the cutting means into the respective operative positions thereof.

The needle holder retaining means may comprise elongated needle holder carrying means with which the needle holder is releasably engageable with its open rearmost end directed outwardly, the carrying means being movable into and out of an operative position holding the needle holder in the aforesaid predetermined position thereof, guide means supporting the carrying means and guiding the carrying means to move into and out of the operative position thereof, locking means for locking the carrying means in the operative position thereof, and biasing means engageable with the needle holder on the carrying means for urging the needle holder to be held in the predetermined position thereof when the carrying means is in said operative position thereof.

The yarn transfer means may comprise air flow inducing means engageable with the passage means for inducing a flow of air from the yarn inlet end of the passage means toward the aforesaid predetermined transitive position of the filament yarn in the passage means for moving the cut segment of the yarn into the transitive position, and drive means for moving the cut segment of the yarn from the transitive position into the needle holder held in the aforesaid predetermined position thereof through a portion of the passage means.

The features and advantages of the apparatus according to the present invention will become more apparent from the following description taken in conjunction with the accompanying drawings, in which:

FIG. 1 is a longitudinal sectional view of an example of a needle holder assembly having a filter element mounted by an apparatus according to the present invention;

FIG. 2 is a side elevational view showing a general arrangement of a preferred embodiment of the apparatus according to the present invention;

FIG. 4 is a side elevational view of the yarn measuring and cutting means depicted in FIG. 3;

Figure 3:
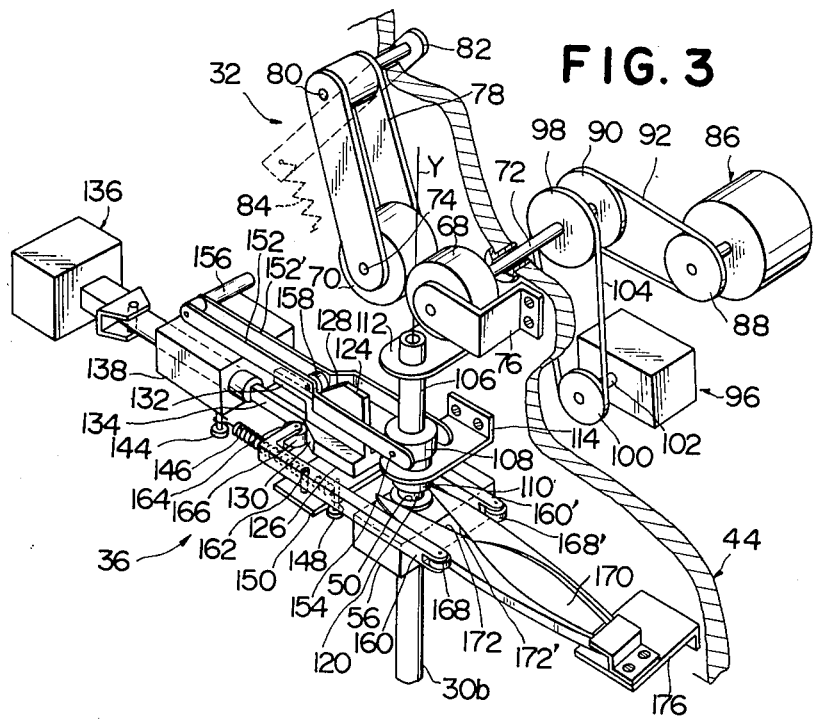
FIG. 3 is a perspective view showing the details of yarn feed means and yarn measuring and cutting means forming part of the embodiment illustrated in FIG. 2.

Referring to the drawings, there is shown in FIG. 1 a representative example of a medical needle holder assembly which is loaded with a filter medium by the use of an apparatus embodying the present invention. The needle holder assembly, designated in its entirety by reference numeral 10, consists of a generally tubular needle holder 12, a filter element 14 and a filter retainer 16. The needle holder 12 is shown comprising a forwardly tapered body portion 18 formed with a flange 20 at its rearmost end and an annular end wall 22 at its foremost end, and a tubular extension 24 projecting forwardly from the annular end wall 22. The body portion 18 of the needle holder 12 has a frustoconical cavity which is open at the flanged rearmost end of the needle holder. The filter element 14 is composed of a wad of a single lengthy filament yarn of synthetic resin and is located in a foremost end portion of the cavity in the body portion 18 of the needle holder 12. The filter retainer 16 has a forwardly tapered body portion 26 and a perforated or otherwise apertured foremost end wall 28 and is snugly received in the body portion 18 of the needle holder 12, holding the filter element 14 in position between the inner face of the annular end wall 22 of the body portion 18 of the needle holder 12 and the outer face of the apertured foremost end wall 28 of the filter retainer 16. Though not shown in the drawings, a piercing needle is fitted to the tubular extension 24 of the needle holder 12 as is customary in the art and the assembly 10 thus carrying the needle is connected to the syringe barrel of a hypodermic syringe or to the adapter of a venoclysis equipment depending upon the purpose for which the needle holder assembly 10 is to be used.

The present invention contemplates provision of an apparatus adapted to have the needle holder 12 loaded with the filter element 14 in the process of production of the needle holder assembly 10 thus constructed. FIG. 2 illustrates a general arrangement of a preferred embodiment of such an apparatus.

Referring to FIG. 2, the apparatus embodying the present invention largely comprises a passage means 30 having yarn inlet and outlet ends (not shown), yarn feed means 32 for conveying a continuous filament yarn Y of synthetic resin from a suitable yarn supply package 34 and introducing the yarn Y into the passage means 30 through the yarn inlet end thereof, yarn measuring and cutting means 36 for measuring the length of the conveyed filament yarn Y and cutting the yarn in a predetermined length in each cycle of operation, needle holder retaining means 38 for holding the above mentioned needle holder 12 (FIG. 1) in a predetermined position having its open rearmost end located at the yarn outlet end of the passage means 30 in each cycle of operation, and yarn transfer means 40 for moving the cut segment of the filament yarn into a predetermined position within the passage means 30 and thereafter from the particular position into the needle holder 12 in the above mentioned predetermined position thereof through the yarn outlet end of the passage means 30. Designated by reference numeral 42 are electric control means for the yarn feed means 32, yarn measuring and cutting means 36 and yarn transfer means 40. All the above mentioned means are supported on a stationary upright supporting board 44. The passage means 30 is constituted by a generally T-shaped hollow transport tube consisting of a straight, elongated horizontal portion 30a and a straight vertical portion 30b extending upwardly from an intermediate part of the horizontal portion 30a. For convenience of description, the transport tube will be hereinafter denoted by the reference numeral 30 because the passage means which has been designated by the particular numeral is, in the embodiment herein illustrated, solely composed of the tube. The horizontal portion 30a of the transport tube 30 has open foremost and rearmost ends 46 and 48 (both seen in FIGS. 8 and 9) while the vertical portion 30b of the tube 30 has an open uppermost end 50 (best seen in FIG. 5). The previously mentioned yarn inlet and outlet ends of the passage means are respectively constituted by the open uppermost end 50 of the vertical portion 30b and the open foremost end 46 of the horizontal portion 30a of the transport tube 30. The transport tube 30 thus arranged is fixed to the front face of the supporting board 44 by means of brackets 52, 54 and 56 which are located adjacent to the open ends 46, 48 and 50, respectively, of the tube 30.

The yarn feed means 32 comprise a guide pin 58 located above the yarn supply package 34 and fixed to the front face of the supporting board 44, tensioning rollers 60 and 62 mounted on an upper end portion of the supporting board 44 by means of brackets 64 and 66, respectively, and a pair of feed rollers 68 and 70 which are arranged in rolling contact with each other above the open uppermost end 50 (FIG. 5) of the vertical portion 30b of the transport tube 30. As illustrated in greater details in FIG. 3, the feed rollers 68 and 70 are rotatable with parallel shafts 72 and 74, respectively, which are normal to the front face of the supporting board 44. The shaft 72 of one feed roller 68 is journalled to the supporting board 44 and is supported by a stationary bracket 76 fixed to the supporting board 44. The shaft 74 of the other feed roller 70 is rotatably supported by a carrier 78 consisting of a pair of spaced parallel carrier arms which are rotatable with a shaft 80 which is journalled to the supporting board 44. The shaft 80 projects from the rear face of the supporting board 44 and is fixedly connected at its leading end to one end portion of a rocking lever 82 extending over the rear face of the supporting board 44 as indicated by broken lines in FIG. 3. A preload spring 84 is anchored at one end to the other end portion of the rocking lever 82 and at the other end to the rear face of the supporting board 44 so that the shaft 80 rotatable with the rocking lever 82 and the carrier 78 about its axis is urged to turn counter-clockwise of FIG. 3, urging the feed roller 70 into pressing contact with the feed roller 68. The shaft 72 carrying the feed roller 68 also projects from the rear face of the supporting board 44 and is operatively connected to the output shaft of an electric motor 86 through a belt and pulley arrangement which consists of a driving pulley 88 rotatable with the output shaft of the motor 86, a driven pulley 90 rotatable with the shaft 72 of the feed roller 68 and an endless belt 92 which is passed on the driving and driven pulleys 88 and 90. The motor 86 is electrically connected to a power source (not shown) across a manually operated switch 94 which forms part of the previously mentioned control means 42 shown in FIG. 2. The belt and pulley arrangement providing the driving connection from the motor 86 to the shaft 72 of the feed roller 68 may be replaced with any other form of torque transmission means such as for example a gear combination or a chain and sprocket arrangement, if desired.

The yarn measuring and cutting means 36 comprise a measuring unit 96 which is adapted to determine the length of the filament yarn Y conveyed by the above described yarn feed means 32 on the basis of the rate at which the yarn Y is passed through the feed rollers 68 and 70. For this purpose, the rotation of the shaft 72 carrying the feed roller 68 is transmitted to the measuring unit 96 by means of a belt and pulley arrangement comprising a driving pulley 98 rotatable with the shaft 72 of the feed roller 68, a driven pulley 100 rotatable with a shaft 102 connected to the measuring unit 96 and an endless belt 104 which is passed on the driving and driven pulleys 98 and 100. The measuring unit 96 has incorporated therein a phototube system or an electromagnetic pickup arrangement though not shown and is operative to produce a train of pulses with a frequency proportional to the rotational speed of the shaft 102 connected thereto. The diameters of the pulleys 98 and 100 are chosen in such a manner that the rotational speed of the shaft 102 bears a predetermined relationship to the rate at which the filament yarn Y is passed through the feed rollers 68 and 70. Each of the time intervals between the individual pulses produced by the measuring unit 96 is therefore representative of a predetermined unit length of the filament yarn Y conveyed by the feed rollers 68 and 70. The measuring unit 96 has further incorporated therein a counter circuit 96a which forms part of the previously described control means 42 shown in FIG. 2. The counter circuit 96a is operative to count the above mentioned pulses and produces an output signal in response to a predetermined number of pulses impressed thereon. Each of the time intervals between the individual output signals thus delivered from the counter circuit 96a is therefore representative of a predetermined length of the yarn filament Y which has been passed through the feed rollers 68 and 70 of the yarn feed means 32. It is apparent that the belt and pulley arrangement associated with the measuring unit 96 may also be replaced with a gear combination or a chain and sprocket arrangement if desired.

As illustrated in FIGS. 3 and 4, the yarn measuring and cutting means 36 further comprise a movable guide tube 106 which is vertically aligned with the vertical portion 30b of the transport tube 30 (FIG. 2) and which is movable up and down above the open uppermost end 50 of the vertical portion 30b of the tube 30. The guide tube 106 is open at its upper and lower ends and is formed with a flange portion 108 and a boss portion 110 below the flange portion 108. The guide tube 106 is vertically movably supported by means of upper and lower brackets 112 and 114 which are fixed to the front face of the supporting board 44. The upper and lower brackets 112 and 114 are formed with holes 116 and 118, respectively, which are vertically aligned with each other, slidably receiving an upper portion of the guide tube 106 in the hole 116 in the upper bracket 112 and the boss portion 110 of the tube 106 in the hole 118 in the lower bracket 114. The guide tube 106 has a lower end portion 120 having an outside diameter slightly smaller than the inside diameter of the vertical portion 30b of the transport tube 30 (FIG. 2) and is biased downwardly by the force of gravity into a position having the lower end portion 120 loosely inserted into the vertical portion 30b of the tube 30, as seen in FIG. 3. When the guide tube 106 is thus in engagement with the vertical portion 30b of the transport tube 30, both have a common vertical axis which is aligned with the line of contact between the feed rollers 68 and 70.

A cam member 122 has a vertical wall portion 124 longitudinally extending perpendicularly to the common axis of the guide tube 106 and the vertical portion 30b of the transport tube 30 and a pair of horizontal wall portions 126 which are symmetrical with respect to the lower longitudinal end of the vertical wall portion 124 although only one of the wall portions 126 is seen in FIGS. 3 and 4. The vertical wall portion 124 of the cam member 122 has an upper cam face 128 downwardly slanting away from the common axis of the guide tube 106 and the vertical portion 30b of the transport tube 30 while the horizontal wall portions 126 of the cam member 122 have respective side cam faces 130 slanting laterally inwardly toward each other away from the above mentioned common axis. The vertical wall portion 124 of the cam member 122 has a horizontal extension 132 having an upper face which is contiguous to the foremost and lowermost end of the upper cam face 128 of the wall portion 124 as seen in FIG. 4. The cam member 122 thus configured is connected to or integral with an actuating rod 134 extending forwardly from the cam member 122. The actuating rod 134 in turn is connected at its foremost end to a plunger (not shown) of a solenoid operated drive unit 136. The solenoid operated drive unit 136 is arranged in such a manner that the plunger thereof is caused to retract and move the actuating rod 134 rearwardly, viz., toward the drive unit 136 when the drive unit is energized. When, thus, the drive unit 136 is energized, the cam member 122 connected to the actuating rod 134 is moved into a position perpendicularly remotest from the common axis of the guide tube 106 and the vertical portion 30b of the transport tube 30. Biasing means is provided to urge the actuating rod 134 away from the drive unit 136 and accordingly urge the cam member 122 toward the above mentioned common axis. The biasing means comprises a guide block 138 formed with a bore 140 passing the actuating rod 134 therethrough and with a longitudinal groove 142 extending along the bore 140 and having closed opposite ends as seen in FIG. 4. The bore 140 in the guide block 138 is, thus, open not only at the opposite ends thereof but through the longitudinal groove 142 which adjoins the bore 140. The biasing means further comprises a pin 144 connected to the actuating rod 134 and projecting out of the above mentioned longitudinal groove 142 and a preloaded tension spring 146 anchored at one end to the pin 144 and at the other end to a stationary pin 148 which is connected to a bracket 150 fixed to the supporting board 44. The tension spring 146 extending in parallel with the actuating rod 134 and the pin 148 on the bracket 150 being located opposite to the drive unit 136 beyond the pin 144 on the actuating rod 134, the pin 144 which is movable in the longitudinal groove 142 in the guide block 138 is urged toward the stationary pin 148 on the bracket 150 by reason of the biasing force of the tension spring 146 so that the actuating rod 134 is urged away from the drive unit 136 and accordingly the cam member 122 is biased toward the common axis of the guide tube 106 and the vertical portion 30b of the transport tube 30. When, thus, the solenoid operated drive unit 136 is de-energized, the actuating rod 134 is held in a position remotest from the drive unit 136 and as a consequence the cam member 122 is held in a position closest to the above mentioned common axis. The solenoid operated drive unit 136 is electrically connected to the previously mentioned counter circuit 96a incorporated into the measuring unit 96 and is energized in response to the output signal delivered from the counter circuit 96a as will be described in more detail. As an alternative to the biasing means comprising the guide block 138 and the tension spring 146, suitable spring means may be provided in the solenoid operated drive unit 136 for biasing the plunger to extend and urge the actuating rod 134 away from the drive unit 136 as in an ordinary solenoid operated drive unit with a spring loaded plunger or core.

The yarn measuring and cutting means 36 further comprise a pair of spaced parallel rocking arms 152 and 152' which are pivotally connected at their rearmost ends to the flange portion 108 of the movable guide tube 106 by a pin 154 perpendicular to the axis of the guide tube 106 and which are connected at their foremost ends to a shaft 156 perpendicularly journalled to the supporting board 44. The rocking arms 152 and 152' are rotatable about the axis of the shaft 156 in vertical planes which are respectively spaced apart in parallel from the side faces of the vertical wall portion 124 of the cam member 122 so that the respective rearmost ends of the arms 152 and 152' are movable up and down. The rocking arms 152 and 152' carry therebetween a roller 158 which is rotatable about an axis normal to the side faces of the arms and which is in rolling contact with the upper cam face 128 of the vertical portion 124 of the cam member 122. The roller 158 thus riding on the upper cam face 128 is caused to climb down the cam face and to rest on the upper face of the horizontal extension 132 of the vertical wall portion 124 as the cam member 122 is moved perpendicularly toward the guide tube 106. When the roller 158 is thus caused to climb down the cam face 128, the rocking arms 152 and 152' are rotated clockwise of FIGS. 3 and 4 about the axis of the shaft 156 by the forces of gravity on the arms 152 and 152' and the guide tube 106 connected to the arms so that the guide tube 106 is allowed to lower so as to have its lower end portion 120 inserted into the vertical portion 30b of the transport tube 30 as illustrated in FIG. 3, thereby providing communication between the passageways in the guide tube 106 and the vertical portion 30b of the transport tube 30. As the cam member 122 is moved perpendicularly away from the guide tube 106, the roller 158 on the rocking arms 152 and 152' is caused to climb up the upper cam face 128 of the vertical wall portion 124 of the cam member so that the rocking arms 152 and 152' are forced to rotate counterclockwise of FIGS. 3 and 4 about the axis of the shaft 156. As a consequence, the guide tube 106 is forced to upwardly move away from the open foremost end 50 of the vertical portion 30b of the transport tube 30, providing a free space between the lower end of the guide tube 106 and the upper end of the vertical portion 30b of the transport tube 30 as seen in FIG. 4. The vertical wall portion 124 of the cam member 122 and the rocking arms 152 and 152' thus provide translatory means for converting the horizontal movement of the cam member 122 into a vertical movement of the guide tube 106.

The yarn measuring and cutting means 36 further comprise a pair of horizontal pressing levers 160 and 160' each of which is generally L-shaped. The pressing levers 160 and 160' have respective rear portions extending on both sides of the open uppermost end 50 of the vertical portion 30b of the transport tube 30 and are pivotally mounted on the previously mentioned bracket 150 by pins 162 only one of which is seen in FIGS. 3 and 4. The pressing levers 160 and 160' are thus rotatable about the pins 162 on both sides of the uppermost end 50 of the vertical portion 30b of the transport tube 30. The pressing levers 160 and 160' further have inwardly bent foremost portions 164 only one of which is seen in FIG. 3. The pressing levers 160 and 160' have carried at the leading ends of their bent foremost portions 164 rollers 166 which have vertical axes of rotation and which are in rolling contact with the side cam faces 130 of the horizontal wall portions 126 of the cam member 122. The pressing levers 160 and 160' are biased by means to be described later to turn about the pins 162 toward angular positions in which the rear portions of the levers are speced widest apart from each other on both sides of the uppermost end 50 of the vertical portion 30b of the transport tube 30 and at the same time the leading ends of the bent foremost portions 164 are located closest to each other with the rollers 166 in contact with the foremost ends of the forwardly and inwardly slanting side cam faces 130 of the horizontal wall portions 126 of the cam member 122, as seen in FIG. 3. The pressing levers 160 and 160' further carry at the rearmost ends thereof rollers 168 and 168', respectively, which have vertical axes of rotation. A scissors-shaped cutter 170 has a pair of horizontal knife portions 172 and 172' which extend along the inner side faces of the rear portions of the above mentioned pressing levers 160 and 160', respectively, and which have knife edges partly superposed on each other and laterally movable toward and away from each other immediately above the open uppermost end 50 of the vertical portion 30b of the transport tube 30. The knife portions 172 and 172' have outer side faces in contact with the rollers 168 and 168' carried at the rearmost ends of the above mentioned pressing rollers 160 and 160', respectively. The knife portions 172 and 172' of the cutter 170 merge into each other through a bifurcated fulcrum portion 174 which is secured to the front face of the supporting board 44 by means of a bracket 176. The fulcrum portion 174 is elastically preloaded to urge the knife portions 172 and 172' laterally away from each other, pressing the knife portions 172 and 172' against the rollers 168 and 168' at the rearmost ends of the pressing levers 160 and 160', respectively. The fulcrum portion 174 of the cutter 170 thus provides the previously mentioned biasing means urging the pressing levers 160 and 160' toward the angular positions having the rearmost ends of the levers spaced widest apart from each other with the rollers 168 and 168' held in rolling contact with the outer side faces of the knife portions 172 and 172', respectively, of the cutter 170. When, thus, the cam member 122 is held in a position perpendicularly closest to the uppermost end 50 of the vertical portion 30b of the transport tube 30, the rollers 166 at the leading ends of the bent foremost portions 164 of the pressing levers 160 and 160' are held in contact with the foremost ends of the side cam faces 130 of the horizontal wall portions 126 of the cam member 122 with the rearmost ends of the pressing levers 160 and 160' spaced widest apart from each other by the spring action of the scissors-shaped cutter 170 as seen in FIG. 3. Under these conditions, the knife portions 172 and 172' of the cutter 170 are allowed to have their knife edges spaced apart from each other above the open uppermost end 50 of the vertical portion 30b of the transport tube 30. When, however, the cam member 122 is moved perpendicularly away from the uppermost end 50 of the vertical portion 30b of the transport tube 30, then the leading ends of the bent foremost portions 164 of the pressing rollers 160 and 160' are forced to be spaced wider apart from each other with the rollers 166 rolling rearwardly on the side cam faces 130 of the horizontal wall portions 126 of the cam member 122 so that the pressing levers 160 and 160' are caused to turn about the pins 162 with the rearmost ends of the levers forced to move closer to each other against the opposing force exerted by the bifurcated fulcrum portion 174 of the scissors-shaped cutter 170. The knife portions 172 and 172' of the cutter 170 are consequently forced to move laterally towardly each other and are superposed on each other above the open uppermost end 50 of the vertical portion 30b of the transport tube 30. When the cam member 122 is thus moved away from the common axis of the movable guide tube 106 and the vertical portion 30b of the transport tube 30, the guide tube 106 is moved upwardly away from the open uppermost end 50 of the vertical portion 30b of the transport tube 30 as previously discussed. The closing movements of the knife portions 172 and 172' of the cutter 170 are therefore not interfered with by the movable guide tube 106.

Figure 5:
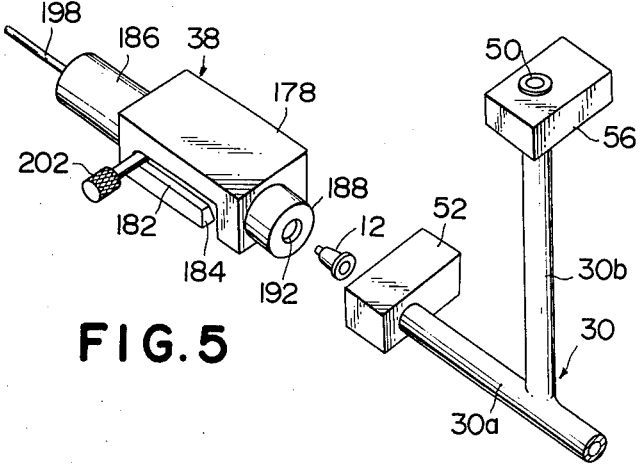
FIG. 5 is a perspective view of the details of needle holder retaining means forming part of the embodiment illustrated in FIG. 2.
Figure 6:
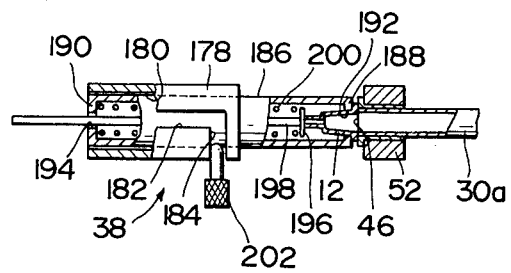
FIG. 6 is a partially cut-away side elevational view of the needle holder retaining means shown in FIG. 5.

Turning to FIGS. 5 and 6, the needle holder retaining means 38 of the apparatus embodying the present invention comprise a supporting and guiding block 178 which is formed with a cylindrical bore 180 having an axis in line with the axis of the horizontal portion 30a of the transport tube 30. The supporting and guiding block 178 is further formed with a longitudinal guide groove 182 and a locking groove 184 extending perpendicularly from the rearmost end of the guide groove 182. The grooves 182 and 184 are contiguous to the cylindrical bore 180 in the block 178. A movable hollow cylinder 186 is longitudinally and circumferentially slidable through the cylindrical bore 180 in the block 178 and has rearmost and foremost end walls 188 and 190 formed with apertures 192 and 194, respectively, which have axes aligned with the axis of the horizontal portion 30b of the transport tube 30. The aperture 190 in the rearmost end wall 188 is so sized as to be capable of receiving therethrough the forwardly tapered body portion 30b of the transport tube 30. The aperture 192 with the flange 20 of the body portion 18 bearing against the outer face of the rearmost end wall 188 as illustrated in FIG. 6. The needle holder 12 thus fitted to the cylinder 186 has its foremost tubular extension 24 projecting forwardly within the cylinder 186 and engages at the leading end of the tubular extension 24 by suitable biasing means provided to urge the needle holder 12 rearwardly of the cylinder 186. Such biasing means are herein shown comprising a spring seat member 196 longitudinally movable within the cylinder 186 toward and away from the rearmost end wall 188 of the cylinder, a guide rod 198 projecting from the front face of the spring seat member 196 and longitudinally extending outwardly of the cylinder 186 through the aperture 194 in the rearmost end wall 190 of the cylinder, and a preloaded spring 200 urging the spring seat member 196 toward the rearmost end wall 188 of the cylinder 186. The preloaded spring 200 is assumed to be helical compression spring which is seated at one end on the spring seat member 196 and at the other end on the annular inner face of the foremost end wall 190 of the cylinder 186. A manipulating pin 202 is connected to the peripheral wall of the cylinder 186 and projects outwardly of the supporting and guiding block 178 through the groove 182 or 184 depending upon the position of the cylinder 186 relative to the block 178. As the manipulating pin 202 is moved back and forth in the longitudinal guide groove 182 in the supporting and guiding block 178, the cylinder 186 is moved rearwardly and forewardly of the block 178, viz., toward and away from the open foremost end 46 of the horizontal portion 30a of the transport tube 30. The rearmost end of the groove 182 is so located as to enable the cylinder 168 to assume its rearmost longitudinal position having the rearmost end wall 188 located in close proximity to the open foremost end 46 of the horizontal portion 30a of the transport tube 30 as indicated in FIG. 6. When the manipulating pin 202 is moved into the locking groove 184 from the rearmost end of the longitudinal guide groove 182, the cylinder 186 is prevented from being moved in longitudinal direction and is thus locked in the above mentioned rearmost longitudinal position thereof.

Figure 7:
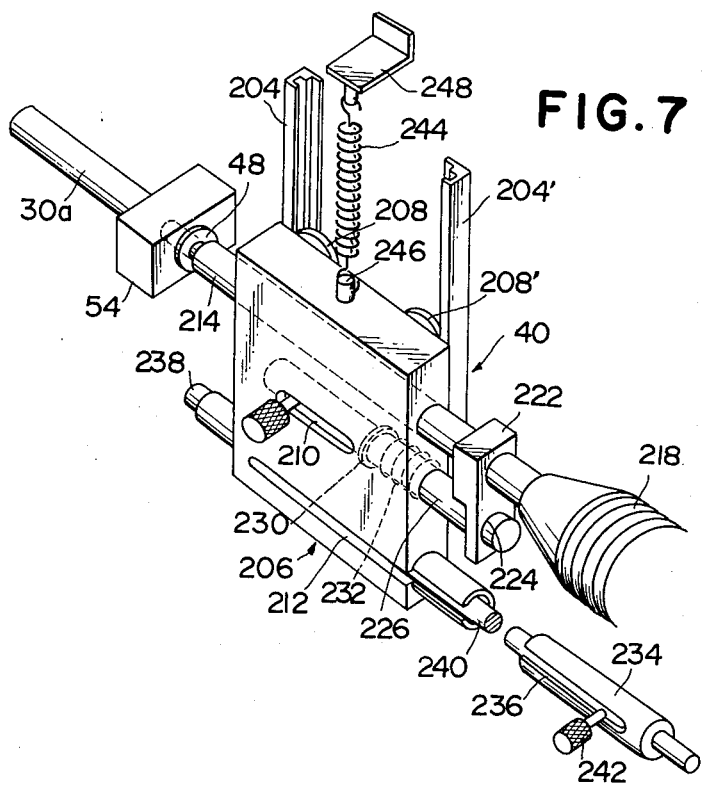
FIG. 7 is a perspective view of the details of yarn transfer means forming part of the embodiment illustrated in FIG. 2.
Figure 8:
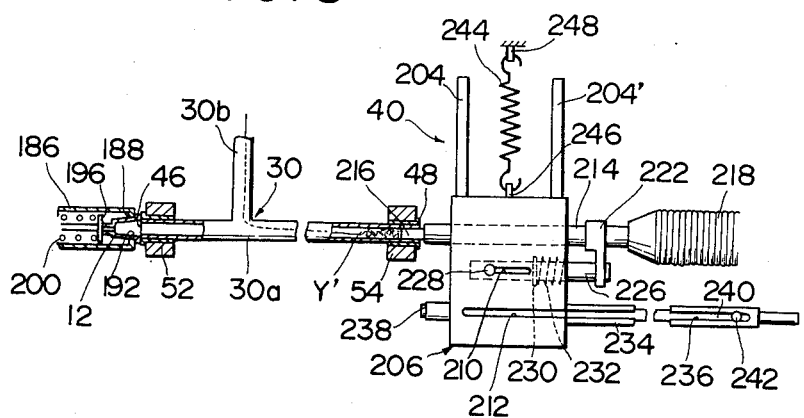
FIGS. 8 and 9 are partially cut-away side elevational views of the yarn transfer means illustrated in FIG. 7.
Figure 9:
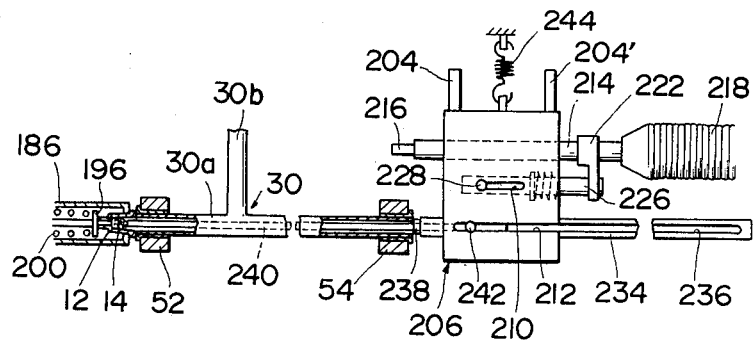

Referring concurrently to FIGS. 7 to 9, the yarn transfer means 40 comprise a pair of spaced parallel vertical guide rails 204 and 204' fixedly mounted on the front face of the supporting board 44 (FIG. 2). The guide rails 204 and 204' have lower end portions located in the neighbourhood of the open rearmost end 48 of the horizontal portion 30a of the transport tube 30. A carrier block 206 has rollers 208 and 208' in rolling engagement with the guide rails 204 and 204', respectively, and is thus movable up and down along the rails between a lowermost position shown in FIGS. 7 and 8 and an uppermost position shown in FIG. 9. The carrier block 206 has a side wall formed with an upper horizontal groove 210 in a vertically moddle portion of the side wall and a lower horizontal groove 212 in a lower end portion of the side wall. The upper horizontal groove 210 is closed at both ends and the lower horizontal groove 212 is closed at the foremost end and open at the rearmost end of the side wall of the carrier block 206. A horizontal suction pipe 214 is longitudinally movable through an upper portion of the carrier block 206 and has a perforated foremost end 216 engageable with the open rearmost end 48 of the horizontal portion 30a of the transport tube 30. When the carrier block 206 is moved into the above mentioned uppermost position illustrated in FIGS. 7 and 8, the suction pipe 214 is brought into alignment with the horizontal portion 30a of the transport tube 30. The suction pipe 214 is connected at its rearmost end to the flexible tube 218 leading from the source 220 of suction which is shown in FIG. 2 as being mounted on the rear face of the supporting board 44. The source 220 of suction is herein assumed to be constituted by an electrically operated vacuum pump which is connected to a power source (not shown) over the previously mentioned switch 94 (FIG. 2) and which is thus started when the switch 94 is closed. The suction pipe 214 has fixedly carried at its portion adjacent the leading end of the flexible tube 218 a bracket 222 directed downwardly from the suction pipe 214. The bracket 222 is formed with a hole 224 in its lower end portion and has fixedly carried therethrough a control rod 226 which is longitudinally slidable through the carrier block 206 in parallel with the suction pipe 214. The control rod 216 is thus longitudinally movable together with the suction pipe 214 over the inner face of the side wall of the carrier block 206. A manipulating pin 228 is securely connected to the control rod 226 and projects outwardly of the side wall of the carrier block 206 through the upper horizontal groove 210 in the side wall. When the manipulating pin 228 is moved back and forth in and along the upper horizontal groove 210, then the control rod 226 and accordingly the suction pipe 214 are moved rearwardly and forwardly through the carrier block 206. If, thus, the manipulating pin 228 is moved to the foremost end of the upper horizontal groove 210 while the carrier block 206 is in the previously mentioned uppermost position thereof, the suction pipe 214 is forwardly moved so that the perforarated forward end 216 of the pipe 214 is inserted into the horizontal portion 30a of the transport tube 30 through the open rearmost end 48 of the portion 30a as seen in FIGS. 7 and 8. The control rod 226 is formed with a flange 230 which is located over the inner face of the side wall of the carrier block 206. A preloaded spring 232, herein shown as a helical compression spring, is seated at one end on this flange 230 and at the other end on the inner face of the rear end wall of the carrier block 206, thereby biasing the control rod 226 and accordingly the suction pipe 214 in forward direction.

The yarn transfer means 40 further comprise a horizontal guide tube 234 which is fixedly mounted on the carrier block 206 and which extends in parallel with the suction pipe 214 and the control rod 226 and in part along the lower horizontal groove 212 in the side wall of the carrier block 206. The guide tube 234 has a short foremost end portion projecting forwardly from the foremost end wall of the carrier block 206 and an elongated rear portion projecting rearwardly from the rearmost end wall of the carrier block 206. The guide tube 234 is formed with a longitudinal groove 236 having a foremost end adjacent the foremost end of the lower horizontal groove 212 in the side wall of the carrier block 206 and a rearmost end adjacent the rearmost end of the tube 234, the groove 236 in the guide tube 234 being in part coextensive with the groove 212 in the carrier block 206. The guide tube 234 has an open foremost end 238 which is engageable with the open rearmost end 48 of the horizontal portion 30a of the transport tube 30. When the carrier block 206 is moved into the previously mentioned uppermost position illustrated in FIG. 9, the guide tube 234 is brought into alignment with the horizontal portion 30a of the transport tube 30. The guide tube 234 is assumed to have an inside diameter which is substantially equal to the inside diameter of the horizontal portion 30a of the transport tube 30. An elongated drive rod 240 is longitudinally slidable through the guide tube 234 and, when the guide tube 234 is aligned with the horizontal portion 30a of the transport tube 30 as above mentioned, also through the horizontal portion 30b of the tube 30. A manipulating pin 242 is connected to the drive rod 240 and projects outwardly of the guide tube 234 through the longitudinal groove 236 in the tube 234. The manipulating pin 242 is thus longitudinally movable in the groove 236 in the guide tube 234 between the rearmost and foremost ends of the groove 236. The lengths of the guide tube 234 and the groove 236, the length of the drive rod 240 and the position of the manipulating pin 242 relative to the drive rod 240 are selected so that the drive rod 240 has its foremost end retracted into the guide tube 234 from the open foremost end 238 of the tube when the manipulating pin 242 is located at the rearmost end of the groove 236 in the tube 234 as seen in FIGS. 7 and 8 and that the drive rod 240 extends throughout the length of the horizontal portion 30a of the transport tube 30 and has its foremost end projecting out of the open foremost end 46 of the horizontal portion 30a of the transport tube 30 when the manipulating pin 242 is located at the foremost end of the groove 236 in the guide tube 234 as seen in FIG. 9. The carrier block 206 is urged upwardly by biasing means comprising a preloaded spring 244 which is anchored at the lower end to a projection 246 formed on the uppermost end wall of the carrier block 206 and at the upper end to a bracket 248 which is secured to the supporting board 44 (FIG. 2). The preloaded spring 244 is herein assumed to be a helical tension spring. Though not shown in the drawings, the carrier block 206 is provided with stop means for limiting the upward and downward movements of the carrier block 206 beyond the previously mentioned uppermost and lowermost positions of the block 206.

When, now, the apparatus thus constructed and arranged is held inoperative, the motor 86 of the yarn feed means 32 and the solenoid operated drive unit 136 of the yarn measuring and cutting means 36 as shown in FIG. 3 are maintained de-energized. All the rotary members of the yarn feed means 32 are accordingly held at rest and at the same time the cam member 122 of the yarn measuring and cutting means 36 is maintained by the force of the preloaded spring 146 in a position perpendicularly closest to the common axis of the movable guide tube 106 and the vertical portion 30b of the transport tube 30. The rocking arms 152 and 152' are therefore held in the lowermost angular positions about the shaft 156 by reason of the forces of gravity on the rocking arms 152 and 152' and the guide tube 106 connected thereto, allowing the guide tube 106 to have its lower end portion 120 received in the vertical portion 30b of the transport tube 30 through the open uppermost end 50 of the portion 30b. On the other hand, the pressing levers 160 and 160' are maintained by reason of the spring action of the scissors-shaped cutter 170 in the positions having the rearmost ends of the levers 160 and 160' spaced widest apart from each other so that the knife portions 172 and 172' of the cutter 170 are spaced apart from each other on both sides of the lower end portion 120 of the guide tube 106 resting on the vertical portion 30b of the transport tube 30. In the needle holder retaining means 38 shown in FIGS. 5 and 6, the cylinder 186 is held in a position remotest from the open foremost end 46 of the horizontal portion 30a of the transport tube 30 with the manipulating pin 202 located at the foremost end of the longitudinal guide groove 182 in the supporting and guiding block 178. The spring seat member 196 is forced against the annular inner face of the rearmost end wall 188 of the cylinder by the force of the preloaded compression spring 200 in the absence of the needle holder 12 at the rearmost end of the cylinder 186. In the yarn transfer means 40 shown in FIGS. 7 to 9, the carrier block 206 may be maintained in a condition suspended by the tension spring 244 with the manipulating pin 228 is located at the foremost end of the rearmost end of the groove 236 in the guide tube 234. The control rod 226 and accordingly the suction pipe 214 are held in their foremost positions by the force of the preloaded compression spring 232 so that the manipulating rod 228 is located at the foremost end of the upper horizontal groove 210 as shown.

Prior to the starting of the apparatus thus conditioned, the filament yarn Y leading from the yarn supply package 34 is passed on the guide pin 58 and the tensioning rollers 60 and 62 and the leading end of the yarn Y is inserted in between the feed rollers 68 and 70, as shown in FIG. 2. In this instance, it is of importance that the tensioning rollers 60 and 62 be adjusted so that the yarn Y is stretched between the rollers 60 and 62 with a tension which is preferably greater than the limit of elasticity of the yarn Y but which will not cause breakage of the yarn Y. Application of such a tension to the yarn Y will produce curls in the yarn when the yarn is afterwards freed of the tension and will therefore facilitate the yarn to be intricately entwined into wad form.

The operation of the apparatus embodying the present invention will be hereinafter described with concurrent reference to FIGS. 2 to 9.

When, now, the switch 94 on the supporting board 44 (FIG. 2) is depressed, the motor 86 of the yarn feed means 32 (FIG. 3) is started to drive the feed roller 68 through the belt and pulley arrangement consisting of the pulleys 88 and 90 and the endless belt 92 and through the shaft 72 carrying the feed roller 68. The feed rollers 68 and 70 in rolling contact with each other are consequently rotated about the respective axes of the shafts 72 and 74 and convey the filament yarn Y from the yarn supply package 34 through the guide pin 58 and the tensioning rollers 60 and 62 at a predetermined rate (FIGS. 2 and 3). The leading end of the filament yarn Y passed through the feed rollers 68 and 70 is downwardly admitted into the guide tube 106 and through the guide tube 106 into the vertical portion 30b of the transport tube 30 (FIG. 3). While the filament yarn Y is thus being fed into the transport tube 30 from the yarn feed means 32, a needle holder 12 is supplied (either manually or in an automatic fashion) to the needle holder retaining means 38 shown in FIGS. 5 and 6. The cylinder 186 of the retaining means 38 is in this condition held in its position remotest from the foremost end 46 of the horizontal portion 30a of the transport tube 30 as previously noted and the needle holder 12 is fitted to the cylinder 186 in such a manner that the forwardly tapered body portion 18 (FIG. 1) of the needle holder 12 is forwardly forwardly inserted through the aperture 192 in the rearmost end wall 188 of the cylinder 186 against the opposing force of the spring 200 in the cylinder. With the needle holder 12 thus carried on the cylinder 186, the manipulating pin 202 is moved rearwardly in the longitudinal guide groove 182 for moving the cylinder 186 toward the open foremost end 46 of the horizontal portion 30a of the transport tube. When the manipulating pin 202 reaches the rearmost end of the longitudinal guide groove 182, then the manipulating pin 202 is moved into the locking groove 184 perpendicular to the guide groove 182 so that the cylinder 186 is locked in its rearmost position closest to the open foremost end 46 of the horizontal portion 30a of the transport tube 30. Under these conditions, the needle holder 12 carried by the cylinder 186 has its flange 20 (FIG. 1) closely interposed between the annular outer face of the rearmost end wall 188 of the cylinder 186 and the foremost end 46 of the horizontal portion 30a of the transport tube 30 and its foremost end closely received on the spring seat member 196, as seen in FIG. 6. The bore in the needle holder 12 is now aligned and in communication with the passageway in the horizontal portion 30a of the transport tube 30. The passageway in the horizontal portion 30a is sealed at its foremost end 46 by the flanged rearmost end of the needle holder 12.

When the switch 94 (FIG. 2) is closed, not only the motor 86 of the yarn feed means 32 is started but the source 220 of suction of the yarn transfer means 40 is initiated into action, developing a suction in the suction pipe 214 through the flexible tube 218 (FIGS. 7 to 9). If, thus, the suction tube 214 is connected to the horizontal portion 30a of the transport tube 30, a forced flow of air is induced in the transport tube 30 from the uppermost end 50 of the vertical porition 30b toward the rearmost end 48 of the horizontal portion 30a of the tube 30 because the passage in the horizontal portion 30a is sealed at the foremost end 46 thereof by the flanged rearmost end of the needle holder 12 as previously noted. For this purpose, the carrier block 206 is moved downward while moving the manipulating pin 228 toward the rearmost end of the upper horizontal groove 210 in the carrier block 206 by a manipulative force against the opposing force of the preloaded compression spring 232 for thereby holding the suction pipe 214 in retracted position thereof. When the carrier block 206 reaches its lowermost position having the suction pipe 214 aligned with the horizontal portion 30a of the transport tube 30 and the manipulating pin 228 is released from the manipulative force, then the suction pipe 214 is moved forwardly together with the control rod 226 by the force of the preloaded compression spring 232 into its foremost position having the perforated foremost end 216 inserted into the horizontal portion 30a of the transport tube 30 through the open rearmost end 48 of the portion 30a, as seen in FIGS. 7 and 8. Due to the flow of air thus induced in the transport tube 30, the filament yarn Y introduced into the tube 30 is urged downward in the vertical portion 30b of the tube and then rearwardly in the horizontal portion 30a of the tube toward the perforated foremost end 216 of the suction pipe 214.

The length of the filament yarn Y fed into the transport tube 30 by the yarn feed means 32 is measured by the length measuring unit 96 of the yarn measuring and cutting means 36 illustrated in FIG. 3. As previously described, the measuring unit 96 is adapted to detect the rotational speed of the feed roller 68 and accordingly the rate at which the filament yarn Y is fed into the transport tube 30 and to produce pulses at a frequency proportional to the detected speed of rotation of the feed roller 68. The pulses are sent to the counter circuit 96a forming part of the control means 42 shown in FIG. 2 and the counter circuit 96a, in turn, delivers a signal representative of a predetermined length of the filament yarn Y fed into the transport tube 30. The signal is fed to the solenoid operated drive unit 136 and causes the plunger of the drive unit 136 to retract, moving the actuating rod 134 and accordingly the cam member 122 perpendicularly away from the common axis of the guide tube 106 and the vertical portion 30b of the transport tube 30 against the opposing force of the preloaded tension spring 146. As a consequence, the roller 158 carried by the rocking arms 152 and 152' is caused to roll upwardly on the upper cam face 128 of the vertical wall portion 124 of the cam member 122 and simultaneously the rollers 166 at the leading ends of the bent foremost portions 164 of the pressing levers 160 and 160' are caused to roll laterally outwardly on the side cam faces 130 of the horizontal wall portions 126 of the cam member 122. The rocking arms 152 and 152' are therefore caused to turn upwardly about the shaft 156 and raises the guide tube 106 away from the open uppermost end 50 of the vertical portion 30b of the transport tube 30 and at the same time the pressing levers 160 and 160' are caused to turn about the pins 148 in directions moving the rearmost end portions of the levers toward each other with the rollers 168 and 168' rolling on the outer side faces of the knife portions 172 and 172' of the scissors-shaped cutter 170. The knife portions 172 and 172' of the cutter 172 are consequently forced to move laterally inwardly against the spring action of the bifurcated fulcrum portion 174 of the cutter 170 and are superposed on each other immediately above the open uppermost end 50 of the vertical portion 30b of the transport tube 30, thereby cutting the filament yarn Y at the open uppermost end 50 and thus producing a cut segment Y' of the yarn in the transport tube 30. When the silament yarn Y is thus cut, the solenoid operated drive unit 136 is de-energized and allows the actuating rod 134 and the cam member 122 to move perpendicularly away from the common axis of the guide tube 106 and the vertical portion 30b of the transport tube 30 by the force of the tension spring 146. The rocking arms 152 and 152' are therefore turned downward about the shaft 156 and the pressing levers 160 and 160' are turned about the pins 162 in directions causing the rearmost end portions of the levers to be spaced wider apart from each other by the spring action of the fulcrum portion 174 of the cutter 170. The knife portions 172 and 172' of the cutter 170 are accordingly spaced apart from each other above the open uppermost end 50 of the vertical portion 30b of the transport tube 30 and at the same time the guide tube 106 is allowed by the force of gravity thereon to lower and has its lower end portion 120 inserted into the vertical portion 30b of the transport tube 30. When the filament yarn Y is cut above the open uppermost end 50 of the vertical portion 30b, the conveyance of the yarn Y may be temporarily interrupted pending the succeeding cycle of operation or may be continued irrespective of the operation of the yarn cutting mechanism being moved into its initial condition. If it is desired that the feeding of the filament yarn Y be stopped pending the succeeding cycle of operation, the motor 86 of the yarn feed means 32 shown in FIG. 3 may be provided with suitable braking means responsive to the signal delivered from the counter circuit 96a (FIG. 2). The braking means may be arranged to be automatically released in response to the motion of the needle holder retaining means 36 or the yarn transfer means 50, though not shown in the drawings.

The cut segments Y' of the yarn is moved to a transitive position ahead of the perforated foremost end 216 of the suction pipe 214 by the flow of air induced in the transport tube 30 by the suction developed in the suction pipe 214 as indicated in FIG. 8. The suction pipe 214 is then disconnected from the horizontal portion 30a of the transport tube 30 by moving the manipulating pin 228 toward the rearmost end of the upper horizontal groove 210 in the carrier block 206 and thereafter the carrier block 206 is moved into its uppermost position illustrated in FIG. 9. When the carrier block 206 is thus held in the uppermost position thereof, the guide tube 234 carried by the block 206 is aligned with the horizontal portion 30a of the transport tube 30 with the drive rod 240 located in the rearmost longitudinal position relative to the guide tube 234. The drive rod 240 is then driven at the manipulating pin 242 to move forwardly through the guide tube 234 and through the horizontal portion 30a of the transport tube 30 with the cut segment Y' of the yarn bearing against the foremost end of the drive rod. When the drive rod 240 is moved throughout the length of the horizontal portion 30a of the transport tube 30, the foremost end of the rod 240 projects into the needle holder 12 forced against the open foremost end 46 of the horizontal portion 30a of the tube 30 so that the cut segment Y' of the yarn is inserted into the needle holder 12 as seen in FIG. 9.

The cut segment Y' of the yarn is entwined within the needle holder 12 so as to form a wad which constitutes a filter element. The drive rod 240 is then moved back toward its rearmost position relative to the guide tube 234 and the cylinder 186 of the needle holder retaining means 38 shown in FIGS. 5 and 6 is moved forwardly through the supporting and guiding block 178 by moving the manipulating pin 202 from the locking groove 184 into the longitudinal guide groove 182 and thereafter forwardly in the guide groove 182. The needle holder 12 is now removed from the cylinder 186 by the force of the compression spring 200 and the cylinder 186 is ready for being loaded with a fresh needle holder.

While only one preferred embodiment of the apparatus according to the present invention has thus far been described with reference to the drawings, it should be borne in mind that such an embodiment is merely illustrative of the gist of the present invention and may therefore be modified and changed in numerous manners if desired.

What is claimed is:

1. Apparatus for loading a generally tubular needle holder with a filter element consisting of a filament yarn of synthetic resin, comprising a passage means having yarn inlet and outlet ends, yarn feed means for conveying a continuous filament yarn of synthetic resin from a yarn supply package and introducing the yarn into said passage means through the yarn inlet end thereof, yarn measuring and cutting means for measuring the length of the conveyed filament yarn and cutting the yarn in a predetermined length in each cycle of operation, needle holder retaining means for holding a needle holder in a predetermined position having an open rearmost end located at the yarn outlet end of said passage means in each cycle of operation, and yarn transfer means for moving the cut segment of the filament yarn into a predetermined transitive position within said passage means and thereafter from the transitive position into the needle holder in said predetermined position thereof through the yarn outlet end of the passage means.

2. Apparatus as set forth in claim 1, in which said yarn measuring and cutting means comprise detecting means for detecting the rate at which the filament yarn is fed into said passage means, signal generating means cooperative with said detecting means for producing a signal representative of said predetermined length of the yarn fed into said passage means, guide means moveable into and out of an operative position connected to the yarn inlet end of said passage means for guiding the yarn to said yarn inlet end when moved into said operative position, cutting means having an operative position in proximity to said yarn inlet end of said passage means and biased toward an inoperative position withdrawn from the vicinity of said yarn inlet end, and actuating means biased to hold said guide means out of said operative position thereof and said cutting means in said inoperative position thereof and responsive to the signal from said signal generating means for moving the guide means and the cutting means into the respective operative positions thereof.

3. Apparatus as set forth in claim 1, in which said needle holder retaining means comprise elongated needle holder carrying means with which the needle holder is engageable with its open rearmost end directed outwardly, said carrying means being movable into and out of an operative position holding the needle holder in said predetermined position thereof, guide means supporting said carrying means for guiding the carrying means to move into and out of the operative position thereof, locking means for locking the carrying means in said operative position thereof, and biasing means engageable with the needle holder on said carrying means for urging the needle holder to be held in said predetermined position thereof when said carrying means is in said operative position thereof.

4. Apparatus as set forth in claim 1, in which said yarn transfer means comprise air flow inducing means engageable with said passage means for inducing a flow of air in said passage means from said yarn inlet end toward said transitive position of the cut segment of the filament yarn for moving the cut segment of the yarn into said transitive position in each cycle of operation, manipulating means for providing engagement between said air flow inducing means and said passage means, and drive means for moving said cut sgement of the yarn from said transitive position into said needle holder in said predetermined position thereof through a portion of said passage means.

5. Apparatus as set forth in claim 1, in which said passage means comprises a transport tube consisting of an elongated horizontal portion having opposite, first and second open ends and a vertical portion upwardly extending from an intermediate part of said horizontal portion and having an open uppermost end, said open uppermost end of said vertical portion and said first open end of said horizontal portion constituting said yarn inlet and outlet ends, respectively, said yarn feed means being operative to downwardly feed said continuous filament yarn into said vertical portion of said transport tube through said open uppermost end.

6. Apparatus as set forth in claim 5, in which said yarn measuring and cutting means comprise detecting means for detecting the rate at which said filament yarn is fed to said vertical portion of said transport tube, signal generating means cooperative with said detecting means for producing a signal representative of a predetermined length of the yarn fed into said vertical portion of said transport tube, a guide tube vertically aligned with said vertical portion and having open uppermost and lowermost ends, said guide tube being vertically movable between a lowermost position connected to said vertical portion and an uppermost position above the open uppermost end of said vertical portion and being toward into said lowermost position for passing therethrough the filament yarn to said vertical portion of said transport tube, cutting means having an operative position immediately above said open uppermost end of said vertical portion and toward into an inoperative position withdrawn from the vicinity of the open uppermost end, and actuating means biased to hold said guide tube in said uppermost position and cutting means in said operative position thereof and responsive to the signal from said signal generating means for moving said guide tube into said uppermost position thereof and said cutting means into said operative position thereof.

7. Apparatus as set forth in claim 6, in which said vertical portion of said transport tube and said guide tube have a common axis and in which said actuating means comprise a cam member movable perpendicularly toward and away from said common axis and having an upper cam face downwardly inclined away from said common axis and a pair of side cam faces which are laterally inwardly inclined toward each other away from said common axis, drive means for moving said cam member perpendicularly toward and away from said common axis, biasing means for urging said cam member toward said common axis, said drive means being responsive to said signal from said signal generating means for moving said cam member perpendicularly away from said common axis against said biasing means, at lease one rocking arm rotatable about a horizontal axis and pivotally connected to said guide tube, said rocking arm being in engagement with said upper cam face for being rotated upwardly and moving said guide tube into said uppermost position thereof when said cam member is moved perpendicularly away from said common axis, and a pair of pressing levers horizontally rotatable about respective axes and engaging each at one end with said cutting means, said pressing levers being respectively in engagement at the other ends with said side cam faces for being rotated about the respective axes thereof in directions to drive said cutting means into said operative position thereof when said cam member is moved perpendicularly away from said common axis by said drive means.

8. Apparatus as set forth in claim 7, in which said cutting means comprise a unitary cutter having a pair of knife portions movable toward and away from each other immediately above said open uppermost end of said vertical portion of said transport tube and respectively in engagement with said pressing levers, and a bifurcated fulcrum portion through which said knife portions merge into each other, said fulcrum portion being elastically preloaded to have said knife portions spaced apart from each other above said open uppermost end of said vertical portion, said knife portions being moved toward and superposed on each other above said open uppermost end when said pressing levers are rotated in said directions.

9. Apparatus as set forth in claim 5, in which said needle holder retaining means comprise a hollow cylinder having one end wall formed with an aperture sized to receive said needle holder therethrough, said cylinder being aligned with said horizontal portion of said transport tube with said end wall directed toward said first open end of the horizontal portion and being longitudinally movable toward and away from said first open end, a supporting and guiding block slidably supporting said cylinder and formed with a guide groove extending in parallel with the direction of movement of said cylinder and a locking groove contiguous and in angled relationship to said guide groove, a manipulating element movable with said cylinder and in said guide and locking grooves, said locking groove being located so that said cylinder is positioned with said end wall thereof located in proximity to said first open end of said horizontal portion of said transport tube when said manipulating element is in said locking groove, and biasing means engageable with the needle holder carried by said end wall of said cylinder for urging the needle holder toward a position aligned with and connected to said first open end when said cylinder is in the position having said end wall in proximity to said first open end.

10. Apparatus as set forth in claim 8, in which said biasing means comprise a seat member longitudinally movable in said hollow cylinder and a preloaded spring urging said seat member toward said end wall of the cylinder.

11. Apparatus set forth in claim 5, in which said yarn transfer means comprise air flow inducing means engageable with said second open end of said transport tube for inducing a flow of air in said transport tube from said uppermost end of said vertical portion toward said second open end of said horizontal portion for moving said cut segment of the filament yarn into said transitive position close to said second open end of said horizontal portion in each cycle of operation, manipulating means for providing engagement between said air flow inducing means and said transport tube, and drive means for moving said cut segment of the yarn from said transitive position thereof into said needle holder in said predetermined position thereof through said horizontal portion of said transport tube.

12. Apparatus as set forth in claim 11, in which said air flow inducing means comprise a source of suction, and a suction pipe in communication with said source of suction and having a perforated leading end, said suction pipe being movable into and out of a vertical position aligned with said horizontal portion of said transport tube and into and out of a longitudinal position engaging said horizontal portion through said second open end when held in said vertical position.

13. Apparatus as set forth in claim 12, in which said manipulating means comprise an elongated rod movable with said suction pipe, a manipulating element secured to said elongated rod for moving said suction pipe into and out of said longitudinal position through said elongated rod, and biasing means for urging said suction pipe into said longitudinal position.

14. Apparatus as set forth in claim 13, in which said drive means comprise a guide tube movable into and out of a vertical position aligned with said horizontal portion of said transport tube, said suction pipe and said guide tube being selectively moved into the respective vertical positions aligned with said horizontal portion of said transport tube, and an elongated drive rod longitudinally movable through said guide tube and through said horizontal portion beyond said first open end when said guide tube is in said vertical position thereof.

15. Apparatus as set forth in claim 14, in which said yarn transfer means further comprise a carrier block movable between a lowermost position and an uppermost position, said suction pipe and said elongated rod being longitudinally movably carried and said guide tube fixedly carried on said carrier block for being moved into said vertical positions respectively thereof when said carrier block is moved into said lowermost and uppermost positions.

16. Apparatus as set forth in claim 14, in which said yarn transfer means further comprise biasing means for urging said carrier block into said uppermost position thereof.

* * * * *